(12) United States Patent
Bousquet et al.

(10) Patent No.: US 6,504,030 B1
(45) Date of Patent: Jan. 7, 2003

(54) POLYMORPHIC FORM OF CLOPIDOGREL HYDROGEN SULPHATE

(75) Inventors: André Bousquet, Sisteron (FR); Bertrand Castro, Kremlin-Bicêtre (FR); Jean Saint-Germain, Sisteron (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 10/177,092

(22) Filed: Jun. 21, 2002

Related U.S. Application Data (63) Continuation of application No. 09/623,333, filed as application No. PCT/FR99/01371 on Jun. 10, 1999, now Pat. No. 6,429,210.

(30) Foreign Application Priority Data

Jun. 15, 1998 (FR) .............................. 98 07464

(51) Int. Cl.[7] .................. C07D 495/04; A61K 31/4365
(52) U.S. Cl. ........................................ 546/114; 514/301
(58) Field of Search ................................. 546/114, 112; 514/301

(56) References Cited

U.S. PATENT DOCUMENTS 4,847,265 A  7/1989  Badorc et al.
5,132,435 A  7/1992  Bousquet et al.

FOREIGN PATENT DOCUMENTS

EP  281 459  2/1987
EP  465 358  7/1990

*Primary Examiner*—Charanjit S. Aulakh
(74) *Attorney, Agent, or Firm*—Paul E. Dupont; Michael D. Alexander (57) ABSTRACT

Novel orthorombic polymorph of clopidogrel hydrogen sulfate or hydrogen sulfate of methyl (+)-(S)-α-(2-chlorophenyl)-4,5,6,7-tetrahydrothieno[3,2-c]pyridine-5-acetate and a process for its preparation

27 Claims, 7 Drawing Sheets

POLYMORPHIC FORM OF CLOPIDOGREL HYDROGEN SULPHATE

This application is a continuation of application Ser. No. 09/623,333 filed Apr. 5, 2001 now U.S. Pat. No. 6,429,210, which in turn is a 35 U.S.C. § 371 application of PCT International Application No. PCT/FR99/01371 filed Jun. 10, 1999.

The present invention relates to a novel polymorph of clopidogrel hydrogen sulfate or the hydrogen sulfate of methyl (+)-(S)-α-(2-chlorophenyl)-4,5,6,7-tetrahydrothieno[3,2-c]pyridine-5-acetate and a process for its preparation. More particularly, the invention relates to the preparation of this polymorph called Form 2 and to the isolation of this compound in this novel crystalline form, as well as to pharmaceutical compositions containing it.

Clopidogrel hydrogen sulfate is a platelet aggregation inhibitor which was described for the first time in EP 281459. The synthetic process claimed in this patent leads to the preparation of clopidogrel hydrogen sulfate which is called Form 1. It has now been discovered that clopidogrel hydrogen sulfate can exist in different polymorphic crystalline forms which differ from each other by their stability, their physical properties, their spectral characteristics and the process for their preparation.

Thus, one of these novel polymorphic forms is the object of the present invention, it is described in the present application and will be named Form 2.

The present invention also relates to a process for the preparation of clopidogrel hydrogen sulfate in its polymorphic Form 2.

Patent EP 281459 describes enantiomers of tetrahydrothienopyridine derivatives and their pharmaceutically acceptable salts. EP 281459 specifically claims clopidogrel hydrogen sulfate, i.e. the dextrorotatory isomer which possesses an excellent platelet aggregation inhibiting activity whereas the levorotatory isomer is less active and less well tolerated. Patent EP 281459, filed ten years ago, makes no reference to the existence of specific polymorphic forms of clopidogrel hydrogen sulfate. The synthesis described in EP 281459 leads to the preparation of the hydrogen sulfate of the polymorph of clopidogrel Form 1. Nor does EP 281459 suggest the existence of different polymorphic forms of clopidogrel or of clopidogrel hydrogen sulfate.

According to all of the teachings of the above documents, the dextrorotatory isomer of clopidogrel is prepared by salt formation from the racemic compound using an optically active acid such as 10-L-camphorsulfonic acid in acetone, followed by successive recrystallisations of the salt until a product with constant rotatory power was obtained, followed by release of the dextrorotatory isomer from its salt by a base. Clopidogrel hydrogen sulfate is then obtained in a standard manner by the dissolution of said base in acetone cooled in ice and addition of concentrated sulfuric acid to precipitation. The precipitate thus obtained is then isolated by filtration, washed and dried to give clopidogrel hydrogen sulfate in the form of white crystals whose melting point is 184° C. and optical rotation +55.1° (c=1.891/CH$_3$OH).

The process described in the prior art leads only to the form 1 of clopidogrel hydrogen sulfate.

Thus, the present invention relates to the polymorphic form called Form 2 of clopidogrel hydrogen sulfate which, like Form 1 of this compound, is useful as a medicine for prophylaxis and the treatment of thrombosis by acting as a platelet aggregation inhibitor. As far as the use of clopidogrel and its salts is concerned, reference may be made to Drugs of the Future, 1993, 18, 2, 107–112. Polymorphic Form 2 of clopidogrel hydrogen sulfate is thus used as active ingredient for the preparation of a medicine, in combination with at least one pharmaceutically acceptable excipient, in the same indications as Form 1.

It has now been found that if clopidogrel hydrogen sulfate is crystallised from a solvent, either the crystalline form, Form 1, corresponding to that of the product obtained according EP 281459 mentioned above may be produced or a new, very stable crystalline form having a well-defined structure designated Form 2 below. More particularly, it has been found that the novel crystalline form of clopidogrel hydrogen sulfate, Form 2, is at least as stable as the Form 1 described and that it does not convert spontaneously into the previously known Form 1. Furthermore, Form 2 bulk solid is more compact and much less electrostatic than Form 1 and may hence be more readily subjected to any treatment under the usual conditions of pharmaceutical technology and, in particular, of formulation on an industrial scale.

It has moreover been observed that Form 2 exhibits a lower solubility than Form 1 as a result of its greater thermodynamic stability.

Figure 5:
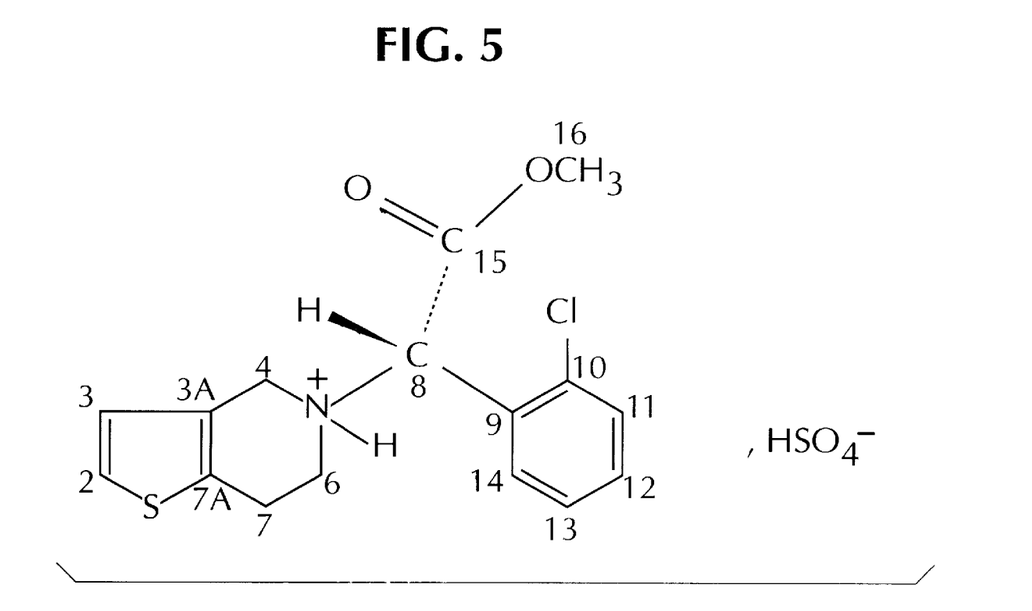
FIG. 5 shows the structural formula of clopidogrel hydrogen sulfate with the numbering of the atoms in the crystalline Form 2.
Figure 6:
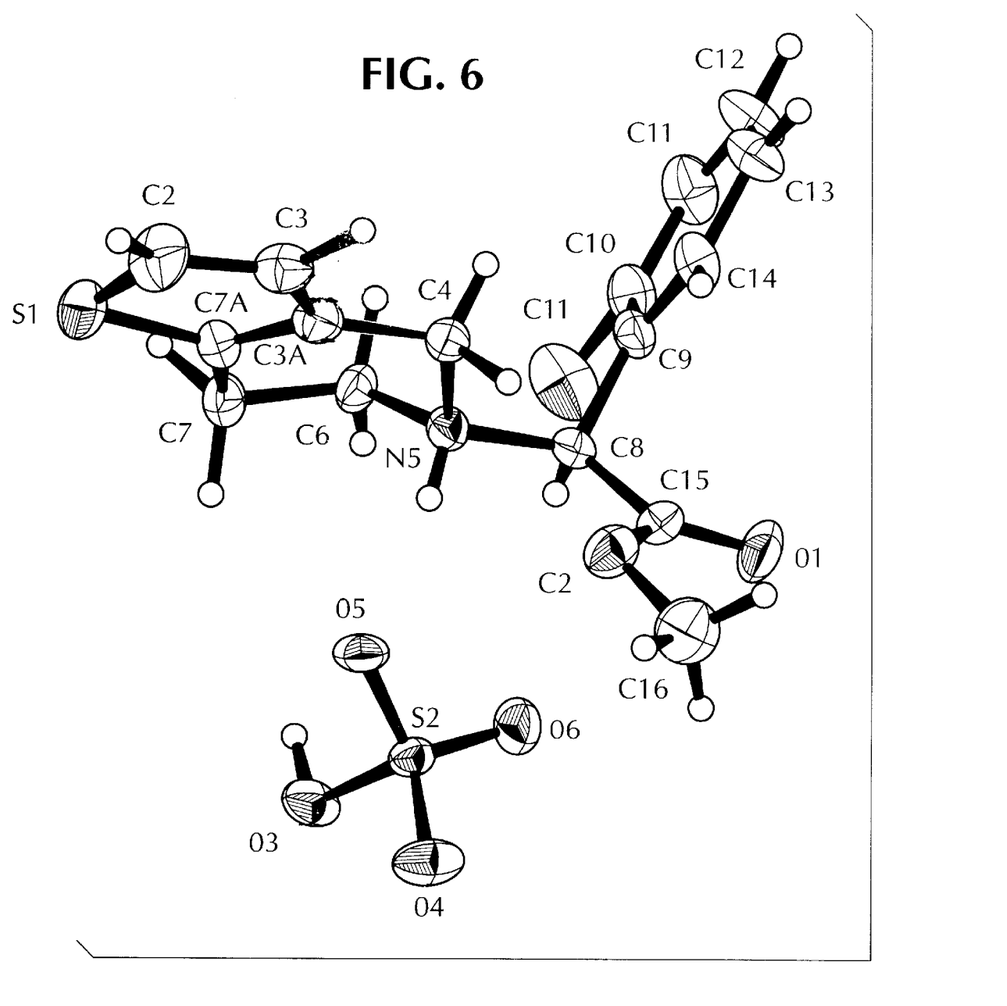
FIG. 6 shows the spatial conformation of Form 2 clopidogrel hydrogen sulfate.
Figure 7:
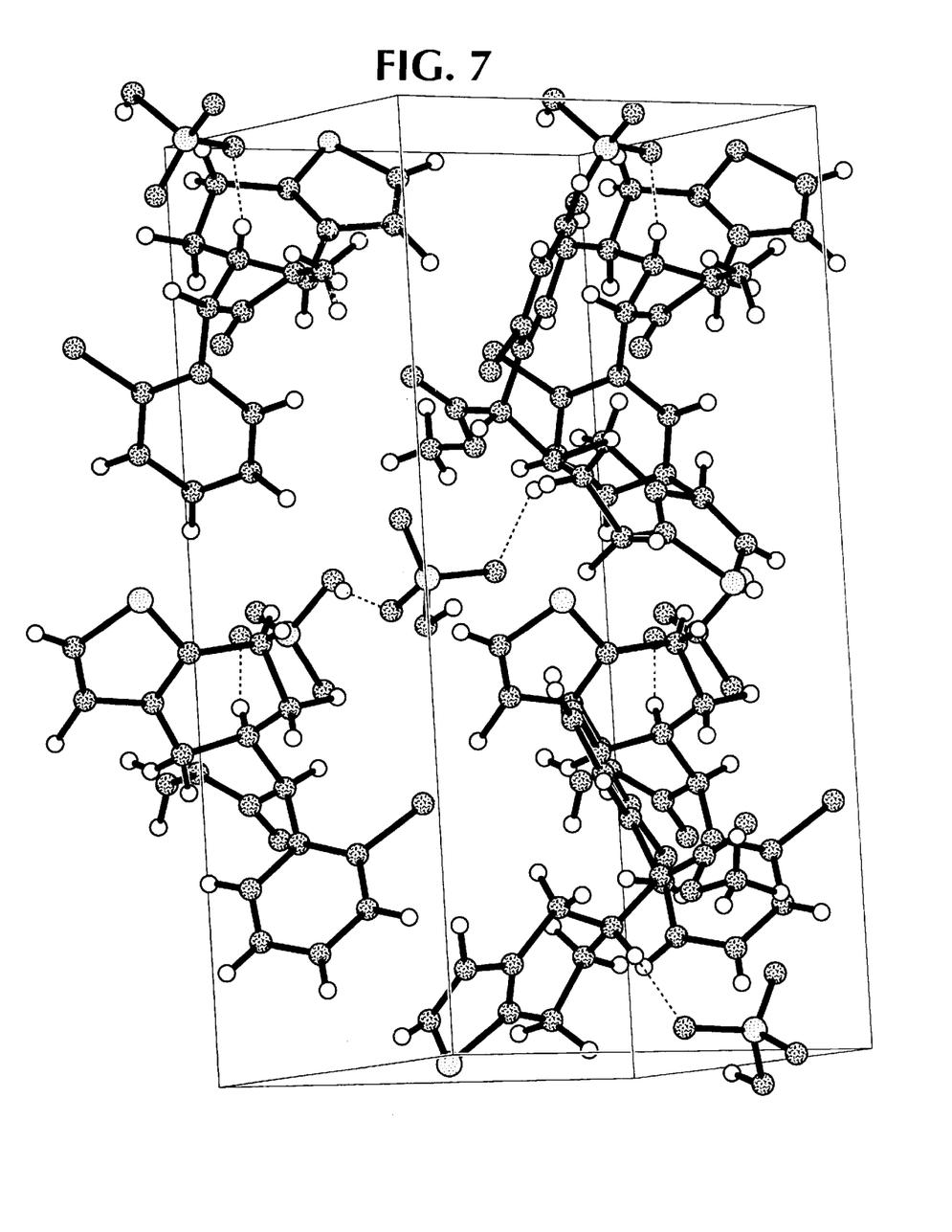
FIG. 7 shows the stacking of the molecules of Form 2 clopidogrel hydrogen sulfate in the unit cell of the crystal.

The difference between the new crystalline form of clopidogrel hydrogen sulfate according to the present invention, Form 2, and Form 1 is apparent on examination of the FIGS. 1 to 4, whereas the FIGS. 5 to 7 demonstrate the structure in the crystals of Form 2.

The FIGS. 1 to 7 are characterised as follows.

It was observed from the crystallographic data that the crystalline structure of Form 1 contains two crystallographically independent cations of clopidogrel and two independent bisulfate anions. The two independent cations are of similar conformation.

The crystallographic data of Form 2 show that it contains one crystallographically independent clopidogrel cation-bisulfate anion pair.

In the two forms, the cations are protonated axially and the nitrogen atom has the R configuration; the conformation of the cations in Form 2 is different from that observed in Form 1.

No site is occupied by solvent molecules in the molecular arrangement of the two crystalline forms.

The arrangement of the anions is very different in the two crystalline structures. The crystalline structure of Form 2 (orthorhombic) is less dense (1.462 g/cm$^3$) than the crystalline structure (monoclinic) of Form 1 (1.505 g/cm$^3$).

According to another feature, the object of the present invention is a process for the preparation of Form 2 of clopidogrel hydrogen sulfate wherein:

(a) methyl (+)-(S)-α-(2-chlorophenyl)-4,5,6,7-tetrahydrothieno[3,2-c]pyridine-5-acetate camphorsulfonate is suspended in an organic solvent, (b) the camphorsulfonic acid is extracted with an aqueous alkaline solution of potassium carbonate and the organic phase is washed with water, (c) the organic phase is concentrated in a vacuum and the concentrated residue is taken up in acetone, (d) 80% sulfuric acid is added, (e) the mixture is heated to reflux, the product crystallises, the mixture is cooled, filtered and the crystals are washed, then dried under reduced pressure to give clopidogrel hydrogen-sulfate Form 1, (f) the resulting mother liquors, yield after a 3 to 6 months period crystals of clopidogrel hydrogen sulfate Form 2.

Furthermore, the invention concerns a process for the preparation of (+)-(S) clopidogrel hydrogen sulfate Form 2 wherein:

the resulting mother liquors of cyrstallisation of Form 1 of (+)-(S) clopidogrel hydrogen sulfate yield after a 3 to 6 months period crystals of clopidogrel hydrogen sulfate Form 2.

The resulting mother liquors of crystallization of Form 1 of (+)-(S) clopidogrel hydrogen sulfate contains from 0.3 to 1% of water.

Those mother liquors contain up to about 10% of clopidogrel hydrogen sulfate, this amount being calculated on the basis of the amount of methyl (+)-(S)-α-(2-chlorophenyl)-4,5,6,7-tetrahydrothieno[3,2-c]pyridine-5-acetate camphorsulfonate used for the transformation into hydrogen sulfate.

The mother liquors yield slowly after a 3 to 6 months period, at a temperature below 40° C., clopidogrel hydrogen sulfate Form 2.

According to another of its features, the present invention relates to another process for the preparation of Form 2 of clopidogrel hydrogen sulfate wherein:

(a) methyl (+)-(S)-α-(2-chlorophenyl)-4,5,6,7-tetrahydrothieno[3,2-c]pyridine-5-acetate camphorsulfonate is suspended in an organic solvent, (b) the camphorsulfonic acid is extracted with an aqueous alkaline solution of potassium carbonate and the organic phase is washed with water, (c) the organic phase is concentrated in a vacuum and the concentrated residue is taken up in acetone, (d) 96% sulfuric acid is added at 20° C. and the solution is seeded with clopidogrel hydrogen sulfate Form 2, (e) the product crystallises, the mixture is cooled, filtered and the crystals are washed, then dried under reduced pressure to give clopidogrel hydrogen sulfate Form 2.

Another alternative consists of subjecting the crystalline suspension to mechanical shearing with the aid of a shearing device. This device may attain a speed of rotation of about 10,000 to 15,000 revolutions per minute. Devices equipped with these characteristics are, for example, of the Turrax® type sold by IKA-Werke (DE).

Furthermore, these devices are suited to the treatment of industrial quantities.

The principle is to obtain by crushing small particles out of a solution which only contains a part of the sulfuric acid. The remaining part of acid will then be added slowly to allow crystal growth. Experiments proceeded starting with the addition of 10% of the amount of the necessary sulfuric acid.

Thus, the object of the present invention is Form 2 of clopidogrel hydrogen sulfate characterised by the X-ray powder diffraction profile given in TABLE I.

More particularly, Form 2 is also characterised by a melting point of 176° C., determined by differential enthalpic analysis (DSC) and by characteristic absorptions in the infrared and in the near infrared.

Some physical properties and the behaviour of the novel crystalline form of clopidogrel hydrogen sulfate according to the invention are completely different from those of Form 1 as was demonstrated by examining the two forms according to standard methods and procedures.

Figure 1:
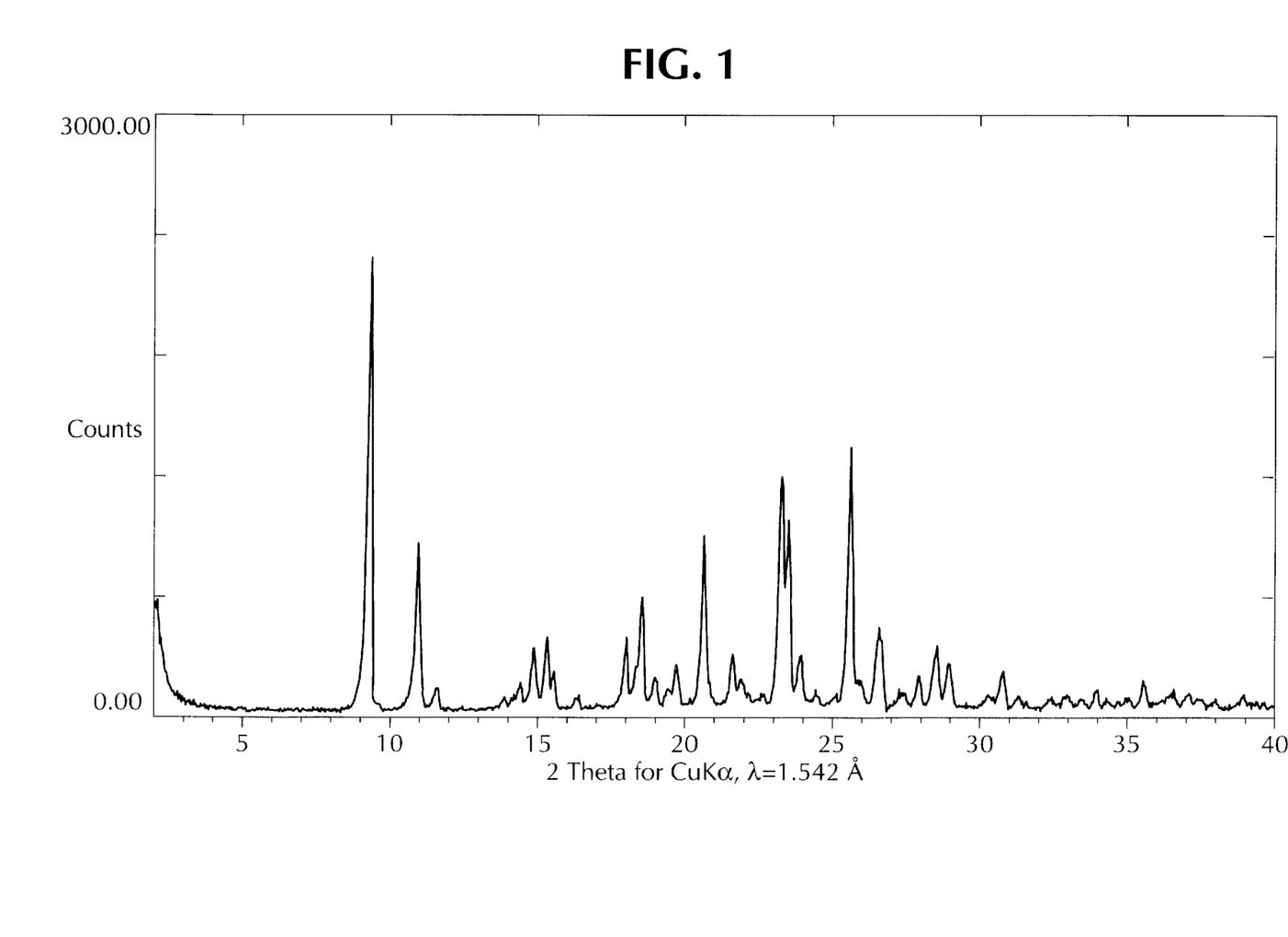
FIG. 1 gives the X-ray powder diffractogram of clopidogrel hydrogen sulfate Form 1.
Figure 2:
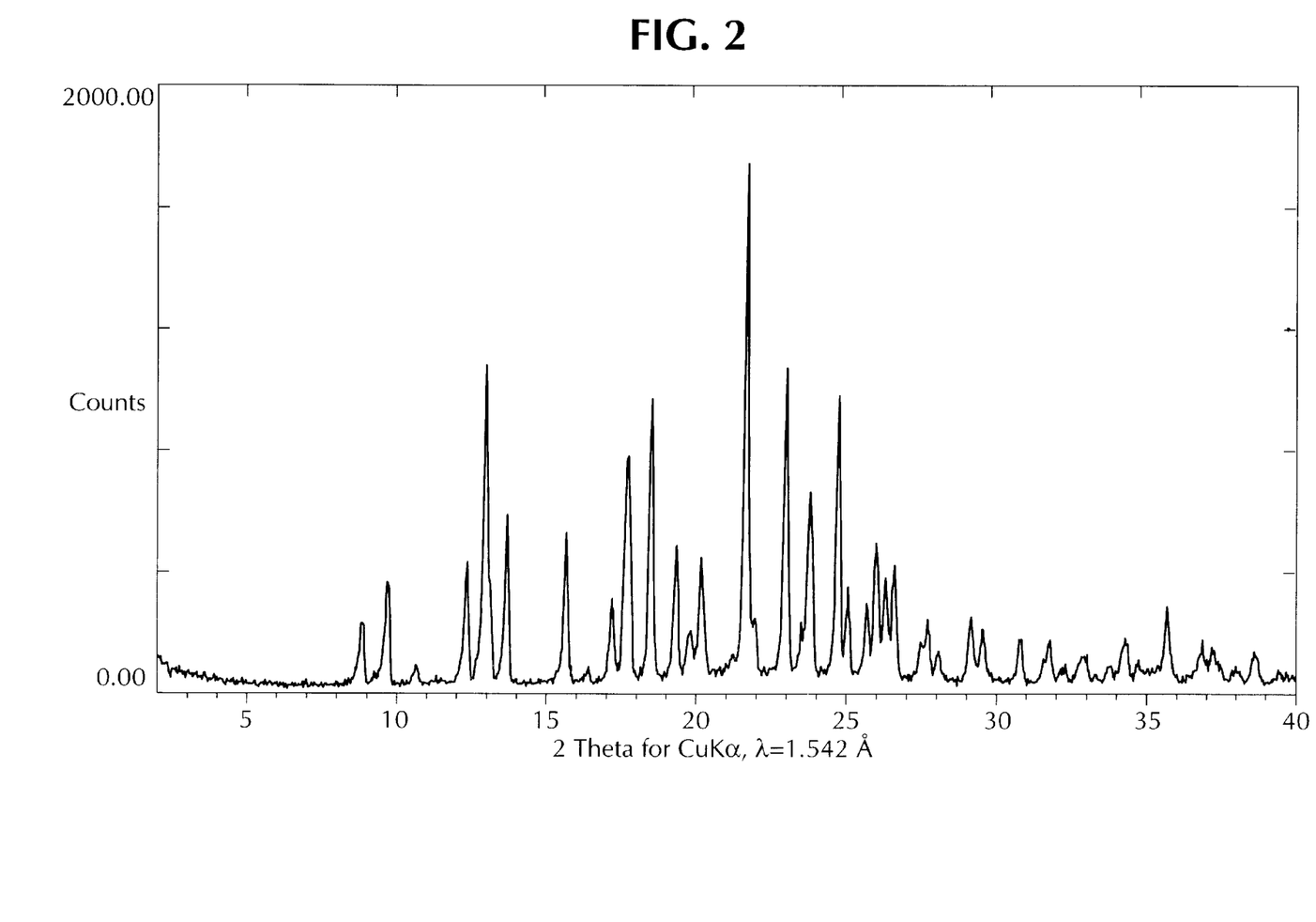
FIG. 2 shows the X-ray powder diffractogram of clopidogrel hydrogen sulfate Form 2.
Figure 3:
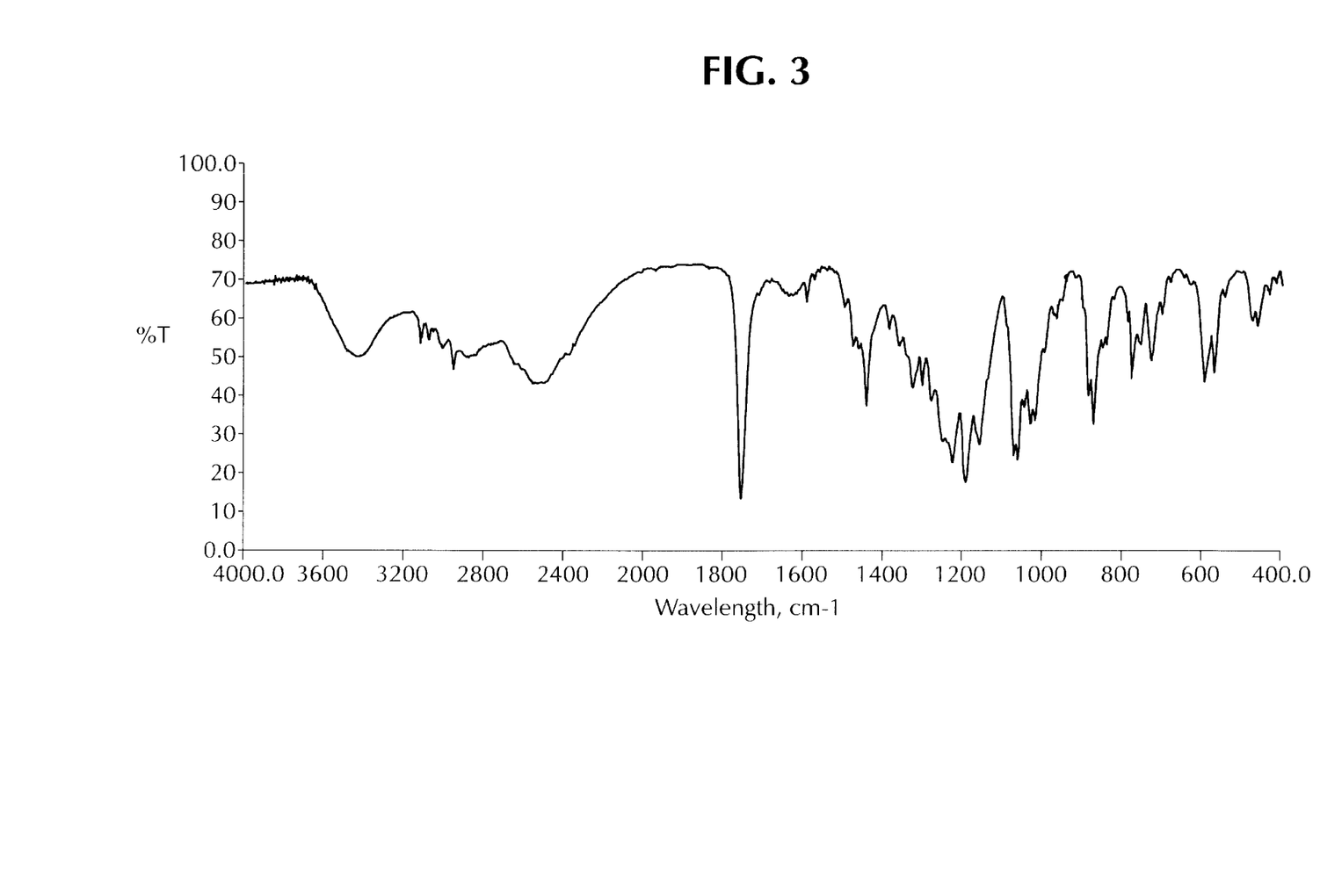
FIG. 3 shows the infrared spectrum of Form 2.
Figure 4:
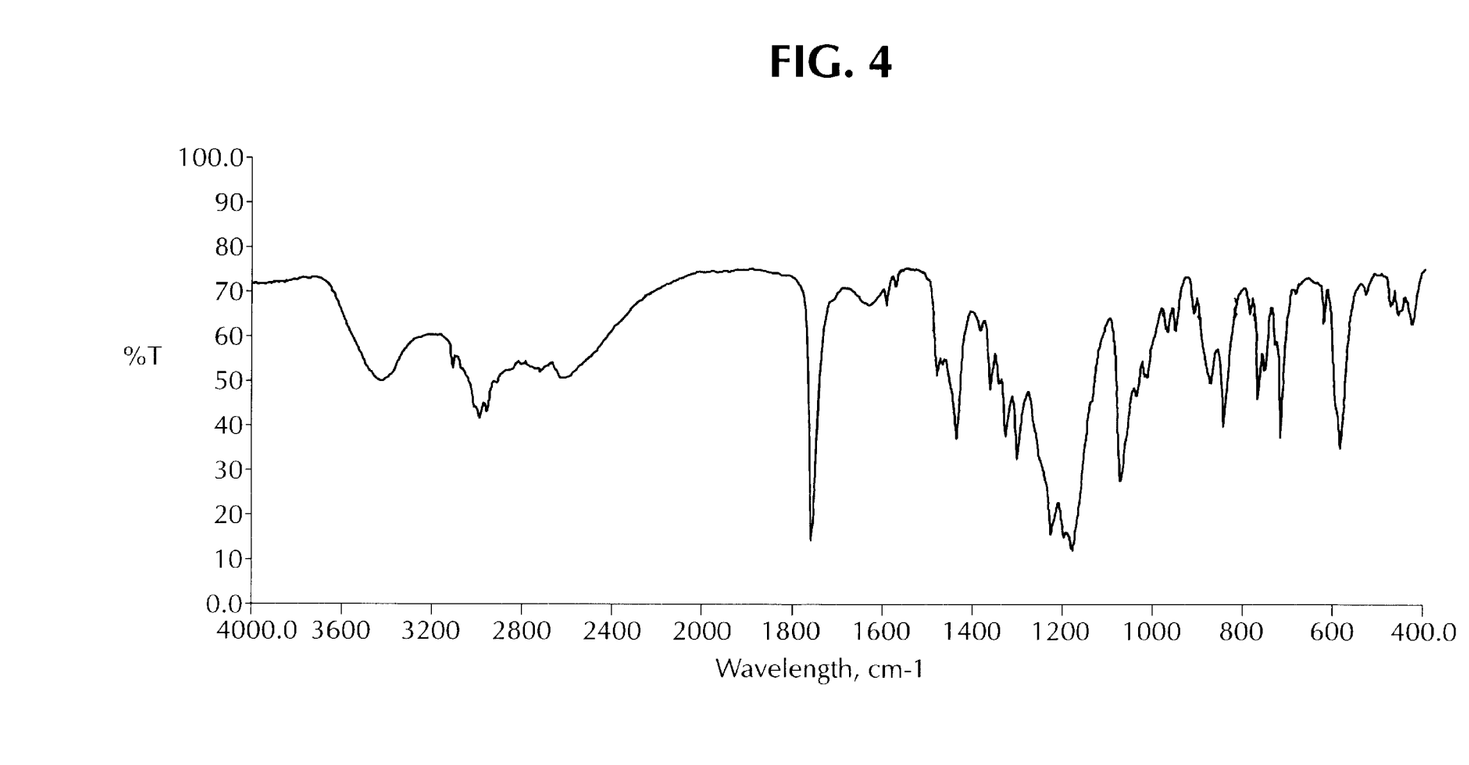
FIG. 4 shows the infrared spectrum of Form 1.

The X-ray powder diffraction profile (angle of diffraction) was determined with a Siemens D500TT diffractometer. The characteristic powder diffractograms between 2 and 40° in $2\theta$ (2 theta, deg., for CuK$\alpha$, $\lambda$=1.542 Å) Bragg angles are shown in FIG. 1 for Form 1 and in FIG. 2 for Form 2. The significant reflections of FIG. 1 are recorded in TABLE II whereas those of FIG. 2 are collected in TABLE I. In TABLES I and II, d is the interlattice distance and $I/I_0$ represents the relative intensity, expressed as a percentage of the most intense reflection.

TABLE I

Form 2
Significant reflections shown in FIG. 2

| d (Å) | $I/I_0$ |
|---|---|
| 4.11 | 100.0 |
| 6.86 | 61.7 |
| 3.87 | 61.4 |
| 3.60 | 56.3 |
| 4.80 | 55.8 |
| 5.01 | 44.4 |
| 3.74 | 37.9 |
| 6.49 | 33.1 |
| 5.66 | 29.8 |

TABLE II

Form 1
Significant reflections shown in FIG. 1

| d (Å) | $I/I_0$ |
|---|---|
| 9.60 | 100.0 |
| 3.49 | 58.8 |
| 3.83 | 52.0 |
| 3.80 | 42.5 |
| 4.31 | 39.0 |
| 8.13 | 37.2 |
| 4.80 | 25.5 |
| 3.86 | 19.1 |
| 5.80 | 16.8 |
| 4.95 | 16.8 |

The differential enthalpy analysis (DSC) of the Forms 1 and 2 was carried out comparatively using a Perkin Elmer apparatus DSC7, calibrated by reference to indium. For the calorimetric analysis 2.899 mg of Form 1 or 2.574 mg of Form 2 were used, as obtained in EXAMPLE 2, in a crimped and pierced aluminium cup in a temperature range from 40° to 230° C. with a rate of heating of 10° C./minute. The melting point and the enthalpy of fusion are indicated in TABLE III. The melting point corresponds to the characteristic melting temperature obtained by DSC. This value may also be defined as being the temperature corresponding to the intersection between the baseline and the tangent to the melting peak curves observed by DSC.

TABLE III

Melting point and enthalpy

| | Form 1 | Form 2 |
|---|---|---|
| Melting point (° C.) | 181.2 | 176.0 |
| Enthalpy of fusion (J/g) | 77 | 87 |

The difference between the new Form 2 and Form 1 of clopidogrel hydrogen sulfate has also been demonstrated by infrared spectroscopy. The Fourier transform (FTIR) IR spectra were obtained with a Perkin Elmer system 2000 spectrometer with a resolution of 4 cm$^{-1}$ from 4000 cm$^{-1}$ to 400 cm$^{-1}$. The samples of Form 1 or Form 2 are prepared in the form of 0.3% KBr disks. The disks were subjected to a compression of 10 tons for 2 minutes. Each sample was examined after 4 accumulated scans.

The comparison of characteristic bands in terms of wavelength (in cm$^{-1}$) and intensity (as percentage of transmittance) is illustrated in TABLE IV.

TABLE IV

Infrared Spectra

| Form 1 | | Form 2 | |
| --- | --- | --- | --- |
| Wavelength (cm$^1$) | % transmittance | Wavelength (cm$^1$) | % transmittance |
| 2987 | 42 | 2551 | 43 |
| 1753 | 14 | 1753 | 13.4 |
| 1222 | 16 | 1497 | 63.7 |
| 1175 | 12 | 1189 | 18 |
| 841 | 40 | 1029 | 33.2 |

TABLE IV shows that Form 2 exhibits characteristic absorptions at 2551 cm$^{-1}$, 1497 cm$^{-1}$, 1189 cm$^{-1}$ and 1029 cm$^{-1}$ which are absent from Form 1.

The particular structure of the crystals of Form 2 was elucidated by single-crystal X-ray diffraction analysis using a MSC-Rigaka AFC6S diffractometer and the software SHELXS-90 and SHELXS-93 at a SG IRIS Indigo work station. The position of the C-H hydrogens was generated at a distance of 0.95 Å. The crystallographic data, in particular the unit cell lengths (a, b, c), the angles ($\alpha$, $\beta$, $\gamma$) and the volume of each unit cell are shown in TABLE V.

TABLE V

Crystallographic data and establishment of the structure of Form 2

| Crystalline system space group | Orthorombic P2$_1$2$_1$2$_1$ |
| --- | --- |
| Dimensions of unit cell: | |
| a | 10.321 (6) Å |
| b | 20.118 (9) Å |
| c | 9.187 (7) Å |
| $\alpha$ | 90 degrees |
| $\beta$ | 90 degrees |
| $\gamma$ | 90 degrees |
| volume | 1908 (2) Å$^3$ |
| Z | 4 |
| density (calculated) | 1.462 g/cm$^3$ |
| collected reflexions | 2134 |
| R factor | 0.0473 |

The atomic coordinates of Form 2 are given in TABLE VI, the bond lengths in TABLE VII, the bond angles in TABLE VIII and the characteristics torsion angles in TABLE IX.

TABLE VI

Position parameters of Form 2

| atom | x | y | z | U (eq) |
| --- | --- | --- | --- | --- |
| Cl (1) | 0.2223(3) | 0.21728(12) | 0.4295(3) | 0.0835(8) |
| S (1) | 0.8085(2) | −0.00068(11) | 0.3557(3) | 0.0724(7) |
| S (2) | 0.2840(2) | 0.01908(8) | 0.0013(2) | 0.0412(4) |
| O (1) | 0.3030(7) | 0.2376(3) | −0.0528(7) | 0.087(2) |
| O (2) | 0.4630(6) | 0.1637(3) | −0.0860(6) | 0.060(2) |
| O (3) | 0.2175(6) | −0.0350(3) | 0.0957(6) | 0.0551(14) |
| O (4) | 0.2728(6) | −0.0093(3) | −0.1432(5) | 0.074(2) |
| O (5) | 0.4174(4) | 0.0241(2) | 0.0497(6) | 0.0503(13) |
| O (6) | 0.2146(5) | 0.0800(2) | 0.0199(7) | 0.065(2) |
| N (5) | 0.4936(6) | 0.1343(3) | 0.1946(7) | 0.0380(14) |
| C (2) | 0.9111(10) | 0.0427(5) | 0.2500(13) | 0.081(3) |
| C (3A) | 0.7214(7) | 0.1002(3) | 0.2215(9) | 0.047(2) |
| C (3) | 0.8554(8) | 0.0950(5) | 0.1824(11) | 0.060(2) |
| C (4) | 0.6332(7) | 0.1548(4) | 0.1706(10) | 0.044(2) |
| C (6) | 0.4750(8) | 0.1100(4) | 0.3487(9) | 0.045(2) |
| C (7) | 0.5487(8) | 0.0450(4) | 0.3722(10) | 0.051(2) |
| C (7A) | 0.6833(8) | 0.0526(3) | 0.3144(9) | 0.050(2) |
| C (8) | 0.3940(8) | 0.1880(4) | 0.1574(9) | 0.043(2) |
| C (9) | 0.4119(7) | 0.2523(3) | 0.2360(9) | 0.044(2) |
| C (10) | 0.3435(8) | 0.2688(4) | 0.3613(10) | 0.057(2) |
| C (11) | 0.3630(10) | 0.3292(4) | 0.4290(11) | 0.076(3) |
| C (12) | 0.4545(10) | 0.3734(4) | 0.3773(12) | 0.080(3) |
| C (13) | 0.5223(10) | 0.3579(4) | 0.2550(12) | 0.067(3) |
| C (14) | 0.5019(8) | 0.2980(3) | 0.1863(10) | 0.052(2) |
| C (15) | 0.3823(8) | 0.1995(4) | −0.0079(11) | 0.053(2) |
| C (16) | 0.4462(16) | 0.1687(6) | −0.2422(11) | 0.096(4) |

TABLE VII

Intramolecular distances in Form 2

| atom | atom | distance |
| --- | --- | --- |
| Cl(1) | C(10) | 1.742(8) |
| S(1) | C(2) | 1.682(12) |
| S(1) | C(7A) | 1.722(8) |
| S(2) | O(6) | 1.429(5) |
| S(2) | O(4) | 1.450(5) |
| S(2) | O(5) | 1.450(5) |
| S(2) | O(3) | 1.551(5) |
| O(1) | C(15) | 1.195(9) |
| O(2) | C(15) | 1.314(10) |
| O(2) | C(16) | 1.448(10) |
| N(5) | C(6) | 1.510(10) |
| N(5) | C(4) | 1.515(9) |
| N(5) | C(8) | 1.530(9) |
| C(2) | C(3) | 1.350(13) |
| C(3A) | C(7A) | 1.341(10) |
| C(3A) | C(3) | 1.432(10) |
| C(3A) | C(4) | 1.501(10) |
| C(6) | C(7) | 1.528(10) |
| C(7) | C(7A) | 1.495(11) |
| C(8) | C(9) | 1.493(10) |
| C(8) | C(15) | 1.541(12) |
| C(9) | C(14) | 1.384(10) |
| C(9) | C(10) | 1.390(11) |
| C(10) | C(11) | 1.379(11) |
| C(11) | C(12) | 1.382(12) |
| C(12) | C(13) | 1.359(13) |
| C(13) | C(14) | 1.378(11) |

The distances are in Angstroms. The standard deviations estimated on the last place of decimals are given in parentheses.

TABLE VIII

The intramolecular bond angles between non-hydrogen atoms

| atom | atom | atom | angle |
|---|---|---|---|
| C(2) | S(1) | C(7A) | 91.2(4) |
| O(6) | S(2) | O(4) | 114.0(4) |
| O(6) | S(2) | O(5) | 112.3(3) |
| O(4) | S(2) | O(5) | 112.6(3) |
| O(6) | S(2) | O(3) | 108.2(3) |
| O(4) | S(2) | O(3) | 101.6(3) |
| O(5) | S(2) | O(3) | 107.3(3) |
| C(15) | O(2) | C(16) | 115.3(9) |
| C(6) | N(5) | C(4) | 110.1(6) |
| C(6) | N(5) | C(8) | 110.6(6) |
| C(4) | N(5) | C(8) | 114.5(5) |
| C(3) | C(2) | S(1) | 113.7(7) |
| C(7A) | C(3A) | C(3) | 113.0(8) |
| C(7A) | C(3A) | C(4) | 122.8(7) |
| C(3) | C(3A) | C(4) | 124.1(8) |
| C(2) | C(3) | C(3A) | 110.7(9) |
| C(3A) | C(4) | N(5) | 109.5(6) |
| N(5) | C(6) | C(7) | 110.2(7) |
| C(7A) | C(7) | C(6) | 108.9(6) |
| C(3A) | C(7A) | C(7) | 124.9(7) |
| C(3A) | C(7A) | S(1) | 111.4(6) |
| C(7) | C(7A) | S(1) | 123.7(6) |
| C(9) | C(8) | N(5) | 114.9(6) |
| C(9) | C(8) | C(15) | 110.9(6) |
| N(5) | C(8) | C(15) | 112.2(7) |
| C(14) | C(9) | C(10) | 117.1(7) |
| C(14) | C(9) | C(8) | 119.9(8) |
| C(10) | C(9) | C(8) | 123.0(7) |
| C(11) | C(10) | C(9) | 120.7(8) |
| C(11) | C(10) | Cl(1) | 117.8(7) |
| C(9) | C(10) | Cl(1) | 121.4(6) |
| C(10) | C(11) | C(12) | 120.7(9) |
| C(13) | C(12) | C(11) | 119.3(9) |
| C(12) | C(13) | C(14) | 120.0(9) |
| C(13) | C(14) | C(9) | 122.2(9) |
| O(1) | C(15) | O(2) | 126.7(9) |
| O(1) | C(15) | C(8) | 119.3(9) |
| O(2) | C(15) | C(8) | 114.0(7) |

The angles are in degrees. The standard deviations estimated on the last place of decimals are given in parentheses.

TABLE IX

Conformation and characteristic torsion angles

| (1) | (2) | (3) | (4) | angle |
|---|---|---|---|---|
| C(7A) | S(1) | C(2) | C(3) | -1.1(9) |
| S(1) | C(2) | C(3) | C(3A) | 0.9(12) |
| C(7A) | C(3A) | C(3) | C(2) | 0.0(12) |
| C(4) | C(3A) | C(3) | C(2) | 177.1(8) |
| C(7A) | C(3A) | C(4) | N(5) | -19.7(11) |
| C(3) | C(3A) | C(4) | N(5) | 163.4(8) |
| C(6) | N(5) | C(4) | C(3A) | 50.2(8) |
| C(8) | N(5) | C(4) | C(3A) | 175.7(7) |
| C(4) | N(5) | C(6) | C(7) | -67.3(8) |
| C(8) | N(5) | C(6) | C(7) | 165.0(6) |
| N(5) | C(6) | C(7) | C(7A) | 47.8(9) |
| C(3) | C(3A) | C(7A) | C(7) | -179.1(8) |
| C(4) | C(3A) | C(7A) | C(7) | 3.8(13) |
| C(3) | C(3A) | C(7A) | S(1) | -0.8(9) |
| C(4) | C(3A) | C(7A) | S(1) | -177.9(6) |
| C(6) | C(7) | C(7A) | C(3A) | -17.6(12) |
| C(6) | C(7) | C(7A) | S(1) | 164.3(6) |
| C(2) | S(1) | C(7A) | C(3A) | 1.1(7) |
| C(2) | S(1) | C(7A) | C(7) | 179.4(8) |
| C(6) | N(5) | C(8) | C(9) | 68.9(8) |
| C(4) | N(5) | C(8) | C(9) | -56.3(10) |
| C(6) | N(5) | C(8) | C(15) | -163.2(6) |
| C(4) | N(5) | C(8) | C(15) | 71.6(8) |
| N(5) | C(8) | C(9) | C(14) | 81.4(9) |
| C(15) | C(8) | C(9) | C(14) | -47.2(10) |
| N(5) | C(8) | C(9) | C(10) | -97.3(9) |
| C(15) | C(8) | C(9) | C(10) | 134.2(8) |
| C(14) | C(9) | C(10) | C(11) | 1.9(12) |
| C(8) | C(9) | C(10) | C(11) | -179.4(8) |
| C(14) | C(9) | C(10) | C(1) | 176.9(6) |
| C(8) | C(9) | C(10) | Cl(1) | -4.4(11) |
| C(9) | C(10) | C(11) | C(12) | -2.6(14) |
| Cl(1) | C(10) | C(11) | C(12) | -177.8(8) |
| C(10) | C(11) | C(12) | C(13) | 3(2) |
| C(11) | C(12) | C(13) | C(14) | -2(2) |
| C(12) | C(13) | C(14) | C(9) | 1.1(14) |
| C(10) | C(9) | C(14) | C(13) | -1.1(12) |
| C(8) | C(9) | C(14) | C(13) | -179.9(8) |
| C(16) | O(2) | C(15) | O(1) | -4.3(13) |
| C(16) | O(2) | C(15) | C(8) | 174.5(8) |
| C(9) | C(8) | C(15) | O(1) | -54.0(10) |
| N(5) | C(8) | C(15) | C(1) | 176.0(7) |
| C(9) | C(8) | C(15) | O(2) | 127.1(7) |
| N(5) | C(8) | C(15) | O(2) | -2.8(9) |

The angles are in degree. The standard deviations estimated on the last place of decimals are given in parentheses.

The sign is positive if, on looking from atom 2 to atom 3, atom 1 is supersposed on atom 4 by a clockwise movement.

The crystallographic study with X rays, in particular the crystallographic data of TABLE I, the atomic coordinates of TABLE VI, the bond lengths of TABLE VII, the bond angles of TABLE VIII and the characteristic torsion angles of TABLE IX prove the structure proposed and illustrated in FIGS. 5 and 6.

The Form 1 crystals are irregular plates and the crystals of Form 2 are agglomerates. Microscopic examination revealed that the crystals of the new Form 2 are morphologically different from those of Form 1.

As it is less electrostatic than Form 1 it is hence particularly suited to the manufacture of pharmaceutical compositions for the treatment of all diseases in which a platelet aggregation inhibitor is indicated.

Thus, according to another of its features, the object of the present invention is pharmaceutical compositions containing as active ingredient Form 2 of clopidogrel hydrogen sulfate characterised by the X ray powder diffraction profile illustrated in TABLE I.

Preferably, Form 2 of clopidogrel hydrogen sulfate according to the present invention is formulated in pharmaceutical compositions by the oral route containing 75 mg of active ingredient per dosage unit, in a mixture with at least one pharmaceutical excipient.

When a solid composition is prepared in the form of tablets, the main active ingredient is mixed with a pharmaceutical vehicle such as gelatin, starch, lactose, magnesium stearate, talc, gum arabic or the like. The tablets may be coated with sucrose or other suitable materials or they may also be treated such that they have a prolonged or delayed activity and so that they continuously release a predefined quantity of active ingredient. A preparation of capsules is obtained by mixing the active ingredient with a diluent and by pouring the mixture obtained into soft or hard capsules.

The powders or granules dispersible in water may contain the active ingredient as a mixture with dispersion agents or wetting agents, or suspending agents like polyvinylpyrrolidone, likewise with sweetening agents or taste correctors.

If it is desired to formulate the active ingredient for rectal administration, recourse is had to suppositories which are prepared with binders melting at the rectal temperature, for example cocoa butter or polyethyleneglycols.

For parenteral administration, aqueous suspensions, saline solutions or sterile and injectable solutions are used.

The active ingredient may also be formulated in the form of microcapsules, optionally with one or more supports or additives.

The following EXAMPLES illustrate the invention without in any way limiting it.

Preparation of methyl (+)-(S)-α-(2-chlorophenyl)-4,5,6,7-tetrahydrothieno-[3,2-c]pyridine-5-acetate camphorsulfonate 400 kg of racemic methyl α-(2-chlorophenyl)-4,5,6,7-tetrahydrothieno[3,2-c]pyridine-5-acetate hydrochloride and 1840 kg of dichloromethane are loaded into a stirred reactor. Then 1200 kg of an 8% aqueous solution of sodium bicarbonate are added slowly. After decantation, the organic phase is concentrated in a vacuum. The concentrated residue is diluted with 1000 liters of acetone. A solution of 154 kg of 1 R-10 camphorsulfonic acid in 620 liters of acetone is added at 20–25° C. The mixture is cooled and methyl α-(2-chlorophenyl)-4,5,6,7-tetrahydrothieno[3,2-c]pyridine-5-acetate camphorsulfonate is crystallised by seeding if necessary. When crystallisation is abundant, the mixture is heated to reflux, then cooled to 25° C. The crystals are then filtered off and washed with acetone, then dried under reduced pressure. Thus, 196 kg of methyl (+)-(S)-α-(2-chlorophenyl)-4,5,6,7-tetrahydrothieno[3,2-c]pyridine-5-acetate camphorsulfonate are obtained, i.e. a yield of 33%.

Preparation of Form 2 clopidogrel hydrogen sulfate

EXAMPLE 1 A 50 g of clopidogrel camphorsulfate prepared as indicated above is introduced into a 250 ml reactor under nitrogen. Dichloromethane, 100 ml, is added and the mixture is stirred for 10 minutes. Then a solution of 9.1 g of potassium carbonate dissolved in 70 ml deionized water is introduced. The organic phase is separated and the aqueous phase is washed several times with dichloromethane. The organic phases are combined and concentrated in a vacuum. 229 ml of acetone is added to the concentrate and the solution is filtered through a $0.1\mu$ to $0.22\mu$ frit. The acetone solution containing the base is loaded into a reactor under nitrogen, and 7.4 g of an 80% sulfuric acid solution is added at 20° C., then the mixture is heated to reflux; crystallisation starts and reflux is maintained for 2 hours.

The solvent is distilled, the residue is cooled to a temperature of 0 to −5° C. and the crystals are filtered off on a Büchner funnel to obtain 21.4 g of Form 2 clopidogrel hydrogen sulfate after drying; m.p.=176±3° C.

EXAMPLE 1 B 1200 kg of clopidogrel camphorsulfate prepared as indicated above is introduced into a 6000 l reactor under nitrogen. Dichloromethane, 2345 l, is added and the mixture is stirred for 30 minutes to 1 hour. Then a solution of 214.5 kg of potassium carbonate dissolved in 1827 l deionized water is introduced. The organic phase is separated and the aqueous phase is washed several times with dichloromethane. The organic phases are combined and concentrated in a vacuum. Acetone is added to the concentrate and the solution is filtered through a $0.1\mu$ to $1\mu$ filtration cartdridge. The acetone solution (3033 l) containing the base is loaded into a reactor under nitrogen, and 264.8 kg of an 80% sulfuric acid solution is added at 20° C.

The solvent is distilled, the residue is cooled to a temperature of 0 to −5° C. and the crystals are filtered off on a Büchner funnel to obtain 779.1 kg of Form 1 clopidogrel hydrogen sulfate after drying; m.p.=184±3° C.

The resulting mother liquors, at a temperature below 40° C., yield after a 3 to 6 months period crystals of clopidogrel hydrogen sulfate Form 2; m.p.=176±3° C.

EXAMPLE 1 C 1200 kg of clopidogrel camphorsulfate prepared as indicated above is introduced into a 6000 l reactor under nitrogen. Dichloromethane, 2345 l, is added and the mixture is stirred for 30 minutes to 1 hour. Then a solution of 214.5 kg of potassium carbonate dissolved in 1827 l deionized water is introduced. The organic phase is separated and the aqueous phase is washed several times with dichloromethane. The organic phases are combined and concentrated in a vacuum. Acetone is added to the concentrate and the solution is filtered through a $0.1\mu$ to $1\mu$ filtration cartdridge. The acetone solution (3033 l) containing the base is loaded into a reactor under nitrogen, and 264.8 kg of an 96% sulfuric acid solution is added at 20° C.

The solvent is distilled, the residue is cooled to a temperature of 0 to −5° C. and the crystals are filtered off on a Büchner funnel to obtain 785.3 kg of Form 1 clopidogrel hydrogen sulfate after drying; m.p.=184±3° C.

The resulting hydroacetonic mother liquors, at a temperature bellow 40° C., yield after a 3 to 6 months period crystals of clopidogrel hydrogen sulfate Form 2; m.p.=176±3° C.

EXAMPLE 2

Dichloromethane, 909 l, and 450 kg of methyl (+)-(S)-α-(2-chlorophenyl)4,5,6,7-tetrahydrothieno[3,2-c]pyridine-5-acetate camphorsulfonate are loaded into a reactor. The camphorsulfonic acid is extracted by means of an aqueous solution of 80 kg of potassium carbonate in 680 l of water. The organic phase is then washed with water. The dichloromethane is concentrated and the concentrated residue is taken up in 1140 liters of acetone. Then, 100 kg of 96% sulfuric acid is added at 20° C. Seeding is performed with 0.3 kg of clopidogrel hydrogen sulfate Form 2 obtained in EXAMPLE 1 B or 1C. Clopidogrel hydrogen sulfate crystallises. It is filtered off, washed with acetone and dried under reduced pressure. Clopidogrel hydrogen sulfate Form 2, 310 kg, is obtained, i.e. a yield of 90.9%; m.p.=176±3° C.

EXAMPLE 3

Dichloromethane, 909 l, and 450 kg of methyl (+)-(S)-α-(2-chlorophenyl)-4,5,6,7-tetrahydrothieno[3,2-c]pyridine-5-acetate camphorsulfonate are loaded into a reactor. The camphorsulfonic acid is extracted by means of an aqueous solution of 80 kg of potassium carbonate in 680 l of water. The organic phase is then washed with water. The dichloromethane is concentrated and the concentrated residue is taken up in 1296 liters of acetone.

The temperature is then stabilised at 20° C. and the Turrax® is set into action. 10% of the global amount of 94–96% sulfuric acid (8.3 kg) is then added in a few minutes. Then 0.012 kg of clopidogrel hydrogen sulfate Form 2 obtain according to examples 1 B or 1C are used for seeding. Clopidogrel hydrogen sulfate Form 2 crystallises. The mixture is left for 45 minutes under the action of Turrax®. The 90% of sulfuric acid at 94–96% (74.6 kg) are then added within 2 hours while Turrax® is still acting. Turrax® is stopped 30 minutes after the acid addition. The mixture is then stirred for 30 minutes at 20° C., filtered, wash with acetone and dried under vacuo.

Then 310 kg of clopidogrel hydrogen sulfate Form 2 are obtained, yield 90.9%; F=176±3° C.

What is claimed is:

1. A process for the preparation of (+)-(S) clopidogrel hydrogen sulfate polymorph Form 2, the x-ray powder diffractogram of which shows characteristic peaks expressed as interplanar distance at approximately 4.11, 6.86, 3.60, 5.01, 3.74, 6.49, and 5.66 Å, which comprises allowing the acetone mother liquors of crystallization of (+)-(S) clopidogrel hydrogen sulfate polymorph Form 1 to stand for a period of 3 to 6 months to yield crystals of (+)-(S) clopidogrel hydrogen sulfate polymorph Form 2.

2. A process according to claim 1 wherein said mother liquors are obtained by reacting an acetone solution of (+)-(S) clopidogrel with 80% sulfuric acid and removing the crystallized (+)-(S) clopidogrel hydrogen sulfate polymorph Form 1.

3. A process for the preparation of (+)-(S) clopidogrel hydrogen sulfate polymorph Form 2, the infrared spectrum of which exhibits characteristic absorptions, expressed in cm$^{-1}$ at 2251, 1497, 1189, and 1029 with respective transmittance percentages of approximately 43, 63.7, 18, and 33.2, which comprises allowing the acetone mother liquors of crystallization of (+)-(S) clopidogrel hydrogen sulfate polymorph Form 1 to stand for a period of 3 to 6 months to yield crystals of (+)-(S) clopidogrel hydrogen sulfate polymorph Form 2.

4. A process according to claim 3 wherein the mother liquors resulting from the crystallization of the polymorph Form 1 of (+)-(S) clopidogrel hydrogen sulfate contain from 0.3 to 1% water.

5. A process according to claim 3 wherein the mother liquors resulting from the crystallization of the polymorph Form 1 of (+)-(S) clopidogrel hydrogen sulfate contain up to about 10% of clopidogrel hydrogen sulfate, this amount being calculated on the basis of the amount of methyl (+)-(S)-α-(2-chlorophenyl)-4,5,6,7-tetrahydrothieno[3,2-c]pyridine-5-acetate camphorsulfonate used for the preparation of the hydrogen sulfate.

6. A process according to claim 3 wherein the mother liquors resulting from the crystallization of the polymorph Form 1 of (+)-(S) clopidogrel hydrogen sulfate are allowed to stand for a period of 3 to 6 months at a temperature below 40° C., to yield clopidogrel hydrogen sulfate Form 2.

7. A process according to claim 3 wherein said mother liquors are obtained by reacting an acetone solution of (+)-(S) clopidogrel with 80% sulfuric acid and removing the crystallized (+)-(S) clopidogrel hydrogen sulfate polymorph Form 1.

8. A process for the preparation of (+)-(S) clopidogrel hydrogen sulfate polymorph Form 2, having a melting point of 176±3° C., which comprises allowing the acetone mother liquors of crystallization of (+)-(S) clopidogrel hydrogen sulfate polymorph Form 1 to stand for a period of 3 to 6 months to yield crystals of (+)-(S) clopidogrel hydrogen sulfate polymorph Form 2.

9. A process according to claim 8 wherein the mother liquors resulting from the crystallization of the polymorph Form 1 of (+)-(S) clopidogrel hydrogen sulfate contain from 0.3 to 1% water.

10. A process according to claim 8 wherein the mother liquors resulting from the crystallization of the polymorph Form 1 of (+)-(S) clopidogrel hydrogen sulfate contain up to about 10% of clopidogrel hydrogen sulfate, this amount being calculated on the basis of the amount of methyl (+)-(S)-α-(2-chlorophenyl)-4,5,6,7-tetrahydrothieno[3,2-c]pyridine-5-acetate camphorsulfonate used for the preparation of the hydrogen sulfate.

11. A process according to claim 8 wherein the mother liquors resulting from the crystallization of the polymorph Form 1 of (+)-(S) clopidogrel hydrogen sulfate are allowed to stand for a period of 3 to 6 months at a temperature below 40° C., to yield clopidogrel hydrogen sulfate Form 2.

12. A process according to claim 8 wherein said mother liquors are obtained by reacting an acetone solution of (+)-(S) clopidogrel with 80% sulfuric acid and removing the crystallized (+)-(S) clopidogrel hydrogen sulfate polymorph Form 1.

13. A process for the preparation of clopidogrel hydrogen sulfate polymorph Form 2 which comprises reacting an acetone solution of (+)-(S) clopidogrel with 94–96% sulfuric acid and seeding the resulting solution with (+)-(S) clopidogrel hydrogen sulfate polymorph Form 2 to effect crystallization of (+)-(S) clopidogrel hydrogen sulfate polymorph Form 2.

14. A process according to claim 13 wherein the acetone solution of (+)-(S) clopidogrel is obtained by extracting a mixture of methyl (+)-(S)-α-(2-chlorophenyl)4,5,6,7-tetrahydrothieno[3,2-c]pyridine-5-acetate camphorsulfonate in an organic solvent with an aqueous solution of potassium carbonate, concentrating the organic phase and taking up the resulting residue in acetone.

15. A process for the preparation of (+)-(S) clopidogrel hydrogen sulfate polymorph Form 2 which comprises reacting an acetone solution of (+)-(S) clopidogrel with 80% sulfuric acid and heating the mixture at reflux to effect crystallization of (+)-(S) clopidogrel hydrogen sulfate polymorph Form 2.

16. A process according to claim 15 wherein the mixture is heated at reflux for about two hours.

17. (+)-(S) Clopidogrel hydrogen sulfate Form 2 prepared by the process of claim 1.

18. (+)-(S) Clopidogrel hydrogen sulfate Form 2 prepared by the process of claim 3.

19. (+)-(S) Clopidogrel hydrogen sulfate Form 2 prepared by the process of claim 8.

20. (+)-(S) Clopidogrel hydrogen sulfate Form 2 prepared by the process of claim 13.

21. (+)-(S) Clopidogrel hydrogen sulfate Form 2 prepared by the process of claim 15.

22. (+)-(S) Clopidogrel hydrogen sulfate Form 2, the x-ray powder diffraction pattern of which shows characteristic peaks, expressed in terms of interplanar distance, at approximately 4.11 and 6.86 Å prepared by the process of claim 1.

23. (+)-(S) Clopidogrel hydrogen sulfate Form 2, the x-ray powder diffraction pattern of which shows characteristic peaks, expressed in terms of interplanar distance, at approximately 4.11 and 6.86 Å prepared by the process of claim 13.

24. (+)-(S) Clopidogrel hydrogen sulfate Form 2, the x-ray powder diffraction pattern of which shows characteristic peaks, expressed in terms of interplanar distance, at approximately 4.11 and 6.86 Å prepared by the process of claim 15.

25. A process according to claim 1 wherein the mother liquors resulting from the crystallization of the polymorph Form 1 of (+)-(S) clopidogrel hydrogen sulfate contain from 0.3 to 1% water.

26. A process according to claim 1 wherein the mother liquors resulting from the crystallization of the polymorph Form 1 of (+)-(S) clopidogrel hydrogen sulfate contain up to about 10% of clopidogrel hydrogen sulfate, this amount being calculated on the basis of the amount of methyl (+)-(S)-α-(2-chlorophenyl)-4,5,6,7-tetrahydrothieno[3,2-c]pyridine-5-acetate camphorsulfonate used for the preparation of the hydrogen sulfate.

27. A process according to claim 1 wherein the mother liquors resulting from the crystallization of the polymorph Form 1 of (+)-(S) clopidogrel hydrogen sulfate are allowed to stand for a period of 3 to 6 months at a temperature below 40° C., to yield clopidogrel hydrogen sulfate Form 2.

* * * * *